US005762890A

United States Patent [19]

Byers et al.

[11] Patent Number: 5,762,890
[45] Date of Patent: Jun. 9, 1998

[54] ZIRCONIUM AND HAFNIUM SEPARATION IN CHLORIDE SOLUTIONS USING CONTINUOUS ION EXCHANGE CHROMATOGRAPHY

[75] Inventors: Charles H. Byers, Knoxville, Tenn.;
Warren G. Sisson, Oak Ridge, Tenn.;
Thomas S. Snyder, Oak Ridge, Tenn.;
Richard J. Beleski, Pittsburgh, Pa.;
Timothy L. Francis, Ogden, Utah;
Umesh P. Nayak, Murrysville, Pa.

[73] Assignee: Westinghouse Electric Corporation, Pittsburgh, Pa.

[21] Appl. No.: 733,893

[22] Filed: Oct. 18, 1996

Related U.S. Application Data

[63] Continuation of Ser. No. 502,994, Jul. 17, 1995, abandoned.

[51] Int. Cl.$^6$ .............................. C01G 25/00; C01G 27/00
[52] U.S. Cl. ........................ 423/70; 423/73; 423/79
[58] Field of Search ........................ 423/70, 73, 79

[56] References Cited

U.S. PATENT DOCUMENTS

2,546,953   3/1951   Street, Jr.
2,759,793   8/1956   Lister et al.
5,023,061   6/1991   Snyder et al. ................ 423/70
5,024,749   6/1991   Snyder et al. ................ 204/299
5,098,678   3/1992   Lee et al. ................ 423/70
5,110,566   5/1992   Snyder et al. ................ 423/70
5,112,493   5/1992   Snyder et al. ................ 210/656
5,160,482   11/1992  Ash et al. ................ 423/74
5,174,971   12/1992  Snyder et al. ................ 423/70

*Primary Examiner*—Steven Bos

[57] ABSTRACT

A method and system for improved ion exchange chromatographic elemental separations of zirconium and hafnium elements and also, if desired, separations of the isotopes thereof from crude zirconium minerals by using improved crude aqueous zirconium (also containing hafnium) chloride feedstock solutions, aqueous chloride eluant solutions, cationic or anionic exchange resins, and reduced ion exchange chromatographic operating temperatures. The method and system of the invention provides improved crude aqueous zirconium chloride feedstock solutions by carbochlorinating zircon sand and hydrolyzing and dissolving the chlorination products under controlled conditions to substantially eliminate cross-polymerization of the carbochlorination products, which undesirably yield inseparable zirconium and hafnium co-polymers during hydrolysis, by inhibiting the hydrolysis exotherm and/or the free acid generation during hydrolysis.

20 Claims, 3 Drawing Sheets

ZIRCONIUM AND HAFNIUM SEPARATION IN CHLORIDE SOLUTIONS USING CONTINUOUS ION EXCHANGE CHROMATOGRAPHY

This application is a continuation of application Ser. No. 08/502,994 filed Jul. 17, 1995, now abandoned.

1. FIELD OF THE INVENTION

The invention generally relates to the field elemental and isotopic separation processes, and more particularly relates to a method and system for continuously, partially or completely, separating zirconium (Zr) and hafnium (Hf) elements from crude zirconium minerals in order to provide nuclear grade zirconium metal and nuclear grade hafnium metal. The invention also relates to a method and system for continuously, partially or completely, separating zirconium and hafnium isotopes from either crude zirconium minerals or from separated and purified solutions of zirconium and hafnium obtained from an elemental separation thereof in order to provide isotopically enriched nuclear grade zirconium metal and hafnium metal.

Even more particularly, the invention relates to improved zirconium and hafnium separation and purification processes whereby zirconium and hafnium are separated in a single operation using continuous ion exchange chromatography by using chloride based solutions having a reduced concentration of relatively inseparable co-polymers of zirconium and hafnium as the feed phase, chloride based eluant solutions as the mobile phase, and either cationic or anionic exchange resins as the stationary phase. Chromatographic processing of zirconium in order to minimize its thermal neutron capture cross-section through alteration of its naturally occurring state enhances the utility of zirconium as a fuel rod cladding material for nuclear reactors. Chromatographic processing of hafnium in order to maximize its thermal neutron capture cross-section through alteration of its naturally occurring state enhances the utility of hafnium as a control rod material for nuclear reactors. The method and system of the invention accordingly improves the stability of zirconium and hafnium as internal materials of construction for nuclear reactors.

2. BACKGROUND OF THE INVENTION

Zirconium metal has historically been used primarily as an internal material of construction for nuclear reactors, for instance, as claddings for uranium oxide nuclear fuel rods. Cladding of nuclear fuel rods, the primary end, provides an outer metallic jacket generally surrounding the nuclear fuel element which serves, inter alia, to prevent corrosion of the fissionable nuclear fuel and release of fission products into the coolant loop. Other attractive applications for zirconium metal are in the fabrication of corrosion-resistant chemical process hardware and advanced ceramics as oxides.

Particularly, materials for use in nuclear reactors are selected for their thermal neutron capture cross-sections, along with other properties. Zirconium is selected in nuclear application for, among other properties, its low average thermal neutron capture cross-section (approx. 0.18 barns), good ductility, good resistance to radiation damage, and excellent corrosion resistance in pressurized hot water of temperatures up to about 350° C. The naturally occurring isotopic distribution of zirconium has a low average thermal neutron capture cross-section which is desirable for certain nuclear reactor materials. The naturally occurring isotopes of zirconium are given in Table 1.

TABLE 1

Naturally Occurring Zirconium Isotopes

| Isotope | Occurrence, % | Thermal Neutron Capture Cross-Section, Barns ($10^{-28}$ m$^2$) |
|---|---|---|
| $Zr^{90}$ | 51.45 | 0.03 |
| $Zr^{91}$ | 11.32 | 1.14 |
| $Zr^{92}$ | 17.49 | 0.21 |
| $Zr^{94}$ | 17.28 | 0.055 |
| $Zr^{96}$ | 2.76 | 0.020 |

However, there has been a continuing interest in reducing the tendency of nuclear grade zirconium to absorb thermal neutrons do to its contamination by neutron opaque hafnium. The more transparent the internal materials of construction of a nuclear reactor are to these thermal neutrons, the more efficiently the nuclear reactor will function since a certain number of these thermal neutrons are required to sustain the neutron triggered fission reactions. Accordingly, it is desirable to reduce the thermal neutron capture cross-section of the internal materials of construction of a nuclear reactor, such as zirconium.

Early efforts at reducing the thermal neutron capture cross-section of zirconium were directed to separating zirconium from hafnium, which by the way are the most difficult elements of the periodic table to separate. The two elements, zirconium and hafnium, occur together naturally, but hafnium has a substantially larger thermal neutron capture cross-section (almost 600 times that of zirconium). Naturally occurring crude zirconium minerals contain typically about 1 to 5% hafnium. Thus the separation of zirconium from hafnium allows for the production of nuclear grade zirconium with a lower average thermal neutron capture cross-section by the elimination of hafnium.

Commercial processes currently available for the production of nuclear grade zirconium are variations of solvent extraction processes wherein zircon sand is converted to zirconium metal as a result of a somewhat involved series of steps. This extraction process requires the use of organic solvents, usually hexone or methyl isobutyl ketone (MIBK), and various aqueous solutions, including thiocyanic acid and hydrochloric acid. Hafnium, which is chemically similar to zirconium, must be separated from the zirconium. Solvent extraction requires a series of separate extraction steps along with separate separation columns. The zirconium, organic solvent and thiocyanate recovered from the hafnium separation steps are usually subject to additional processing to make sure that as much zirconium is recovered from the system as possible.

The zirconium ultimately recovered from most solvent extraction processes is in the form of pure zirconium oxide ($ZrO_2$). In the commonly used commercial process, the zirconium oxide is then chlorinated to form zirconium tetrachloride ($ZrCl_4$), which is purified and then subjected to Kroll reduction to produce zirconium metal suitable for nuclear applications. The aqueous and organic liquids used in the process typically include waste metals and other materials that must be properly discarded. One of the methods of treating these liquid wastes is to place them in holding ponds for future treatment and remediation. However, this is increasingly becoming an unacceptable waste management solution, particularly since federal and state laws relating to land ban chemicals and waste disposal have become more stringent.

The solvent extraction processes effectively separate zirconium from hafnium to produce zirconium of the quality required for use in nuclear reactors and elsewhere in the nuclear industry. However, the increasing concern expressed by the public, the scientific community and the regularity agencies regarding the waste generated by solvent extraction processes has lead the nuclear industry to explore alternative zirconium production methods which do not present the same waste management concerns.

Other zirconium and hafnium separation processes in addition to the aforementioned solvent extraction processes have been proposed. Recent effort to minimize organic wastes have proposed aqueous techniques for the separation of zirconium from hafnium and also for the potential separation of zirconium and hafnium isotopes therefrom by using continuous, steady-state, ion exchange chromatography in a continuous annular chromatograph (CAC) as taught in, for example, U.S. Pat. Nos. 5,023,061 (Snyder, et al.), 5,024, 749 (Snyder, et al.), 5,098,676 (Lee, et al.), 5,110,566 (Snyder, et al.), 5,112,493 (Snyder, et al.), and 5,174,971 (Snyder, et al.).

These cited patents teach continuous methods and systems for simultaneously separating and purifying zirconium from hafnium and/or potentially simultaneously isolating the fairly abundant low thermal neutron capture cross-section isotopes of zirconium and the high thermal neutron capture cross-section isotopes of hafnium in a single operation. While each of these teachings are technically feasible, optimization of the process for greater efficiency, lower waste generation, and lower costs cannot be adduced therefrom. What is needed is a method and system for chromatographically separating zirconium from hafnium in a single operation using optimized processing parameters which provide for commercially important operations.

Commercially acceptable zirconium and hafnium separations in a CAC using aqueous chloride based feedstock solutions (obtained from aqueous hydrolysis of the carbo-chlorination products of zircon sand), aqueous chloride based eluant solutions, and cationic or anionic exchange resins have proved to be elusive. Zirconium product purity of less than 50 ppm Hf in Zr, zirconium product concentrations of greater than 15 g/l Zr, and product yields of about 90% have been unobtainable using conventional chloride based solutions in the CAC.

The conventional crude chloride feedstock solutions typically used to support continuous ion exchange chromatographic Zr and Hf processes, as taught in the above cited patents, are those obtained from dissolving halogenated crude zircon, i.e., zirconium tetrachloride ($ZrCl_4$) and hafnium tetrachloride ($HfCl_4$), in aqueous solution at room temperature to produce a solution of zirconium ions and also some hafnium ions amenable to ion exchange chromatographic separation techniques. Crude zirconium which also contains about 1 to 5% hafnium is commercially obtained by chlorinating crude zircon sand ($ZrSiO_4$) in the presence of a carbon source, such as coke, at temperatures of about 1000° C. and separating the resulting zirconium tetrachloride ($ZrCl_4$) fraction (which also contains $HfCl_4$) from the resulting silicon tetrachloride by a differential condenser. The zirconium fraction typically contains a natural distribution of zirconium isotopes in the form of zirconium tetrachloride and also contains hafnium tetrachloride. Both compounds are then readily hydrolyzed in aqueous solution at room temperature to yield crude zirconium oxychloride ($ZrOCl_2$) and also hafnium oxychloride ($HfOCl_2$) which, in turn, further dissolves or dissociates in aqueous solutions to yield crude feedstock solutions of zirconium and hafnium ions, e.g., $ZrO^{2+}$ and $HfO^{2+}$ (cations), or $ZrOCl_4^{2-}$ and $HfOCl_4^{2-}$ (anions), etc. These aqueous ionic feedstock solutions are then suitable for use in an ion exchange chromatographic process for the separation of elemental zirconium from elemental hafnium and for the separation of zirconium isotopes therefrom to produce nuclear grade materials.

However, it is difficult to separate effectively and isolate nuclear grade zirconium from hafnium, and also to effectively separate and selectively isolate the low neutron capture cross-section isotopes of zirconium or the high neutron capture cross-section neutron isotopes of hafnium from a feedstock of ionic zirconium compounds and hafnium compounds obtained from aqueous hydrolysis of a mixture of crude $ZrCl_4$ and $HfCl_4$. The aqueous hydrolysis reaction of crude $ZrCl_4$ and $HfCl_4$, typically performed at ambient starting temperatures, which is used to form the conventional aqueous metal complexed chloride feedstock solutions to support a continuous, steady-state, ion exchange chromatographic separation of zirconium from hafnium and/or separation of zirconium isotopes or hafnium isotopes, is a highly exothermic reaction. Moreover, the hydrolysis exotherm tends to drive a cross-polymerization side reaction between the resultant $ZrOCl_2$ and $HfOCl_2$ to form co-polymers thereof, which are highly undesirable. These cross-polymerization side reactions tend to form inseparable zirconium and hafnium co-polymer complexes. And, these inseparable zirconium and hafnium co-polymer complexes, once formed, impair the separation of the zirconium and hafnium, and the separation of isotopes thereof, which consequently diminishes the overall quality of the resultant nuclear grade zirconium and hafnium materials.

What is needed is an improved method and system for continuously separating and purifying, partially or completely, zirconium from hafnium, and also, if desired, for continuously and selectively, partially or completely, separating isotopes of zirconium and hafnium, by using improved aqueous chloride-based feedstock solutions and eluant solutions, and improved operating conditions to support continuously operating, steady-state, ion exchange chromatographic separation techniques, while inhibiting the formation of inseparable zirconium and hafnium co-polymer complexes during aqueous feedstock preparation and also during chromatographic processing of the feedstock solutions to improve the overall quality of the resultant nuclear grade zirconium and hafnium materials in terms of product concentrations, purities, and/or yields, and while also eliminating organic reagents and liquid waste discharges.

Accordingly, the present invention addresses design improvements in order to improve the overall quality of the resultant nuclear grade materials in terms of: greater purifications, greater concentrations, greater yields, greater efficiencies, simpler process designs, lower operating costs, lower waste generations, and others.

3. SUMMARY OF THE INVENTION

It is an object of the invention to provide an improved continuously operating, steady-state, ion exchange chromatographic method and system for the separation and purification of crude zirconium into zirconium and hafnium fractions and/or into distinct isotope fractions thereof which yield improved separations of zirconium and hafnium, and, consequently, yield improved nuclear quality zirconium and hafnium metals, while also reducing the waste generation and operating costs of prior methods and systems.

It is a further object of the invention to provide an improved method and system for the separation and purification of zirconium from hafnium using continuous, steady-state, ion exchange, chromatographic separation techniques based on chloride solutions by using improved aqueous zirconium (also containing hafnium) chloride feedstock solutions as the feed phase and aqueous chloride eluant solutions as the mobile phase, and separating the materials on either cationic or anionic exchange resins as the stationary phase.

It is another object of the invention to provide an improved method for the preparation of crude aqueous ionic zirconium and hafnium chloride feedstock solutions for introduction into a continuously operating, steady-state, ion exchange chromatographic method and system to support the separation of crude zirconium into zirconium and hafnium fractions and/or into distinct isotope fractions therefrom which yield improved concentrations, purities and yields of nuclear grade zirconium and hafnium.

It is a feature of the invention to control the hydrolysis exotherm and/or the free acid generation during the preparation of the crude aqueous ionic zirconium and hafnium chloride feedstock solutions which are ultimately fed into a continuously operating, steady-state, ion exchange chromatographic separation column to eliminate the cross-polymerization reactions of zirconium and hafnium and to yield nuclear quality zirconium and hafnium. Otherwise inseparable zirconium and hafnium co-polymers and inordinate wastes will be formed. Historically, aqueous ionic zirconium chloride feedstock preparation conditions have impaired the chromatographic separations of zirconium from hafnium.

In one aspect, the invention resides in an improved continuous method and system for separating and purifying zirconium from hafnium with a substantial reduction in the formation of zirconium and hafnium co-polymers and a substantial improvement in the product concentrations, purities, and yields, which is characterized by: (A) preparing a crude aqueous chloride feedstock solution of zirconium and hafnium ions as the feed phase with a substantial elimination of cross-polymerization of zirconium and hafnium side reactions; (B) loading the feed phase of the aqueous chloride feedstock solution of zirconium and hafnium ions to a continuously operating, steady-state, ion exchange chromatographic column containing an ion exchange resin as the stationary phase, such as either cationic or anionic exchange resins; (C) feeding an aqueous chloride eluant solution as the mobile phase, such as HCl, to the column to elute the feedstock solution from the ion exchange resin; and, (D) separately collecting a substantially pure zirconium fraction, a substantially pure hafnium fraction and at least two waste fractions. The method and system can also further be characterized by: (E) separately processing the zirconium fraction and the hafnium fraction to produce nuclear quality zirconium and hafnium metal; (F) volume reducing the waste fractions for disposal; (G) recycling the eluant solution for reuse in step (C); and, (H) optionally recycling a mixed zirconium and hafnium fraction for reuse in step (B). The method and system of the invention can also further be characterized by: (I) separately processing the separated and purified zirconium fraction and hafnium fraction of step (D) to produce isotopically enriched nuclear quality zirconium and hafnium.

It is preferred that the zirconium and hafnium separations are conducted in a continuous annular chromatograph (CAC) device which operates in a continuous and steady-state manner. It is also preferred that the zirconium and hafnium separations are carried out at a reduced temperature of about 0° C. to 5° C. to additionally improve the zirconium and hafnium separation kinetics.

In another aspect, the invention resides in an improved method for the preparation of crude aqueous ionic zirconium and hafnium chloride feedstock solutions with the substantial elimination of inseparable zirconium and hafnium co-polymers which are used to support ion exchange chromatographic processing. The improved feedstock solutions can be prepared by at least three alternative methods, which are characterized by either: (A) (i) chlorinating zircon sand ($ZrSiO_4$) in the presence of carbon, such as coke, at about 800° C. to 1200° C., to produce a crude zirconium tetrachloride ($ZrCl_4$) fraction which also contains hafnium tetrachloride ($HfCl_4$) fraction and a silicon tetrachloride ($SiCl_4$) fraction; (ii) selectively isolating the $ZrCl_4/HfCl_4$ fraction from the $SiCl_4$ fraction; (iii) partially hydrolyzing the crude $ZrCl_4/HfCl_4$ fraction in water ($H_2O_{(l)}$) at a reduced temperature of about 10° C. to 25° C. to produce an anhydrous zirconium oxychloride ($ZrOCl_2$) which also contains hafnium oxychloride ($HfOCl_2$) fraction and a HCl fraction; (iv) selectively removing the HCl fraction for reuse; (iv) completely dissolving the $ZrOCl_2/HfOCl_2$ fraction in water or aqueous acid, such as HCl, to form the aqueous chloride feedstock solution of zirconium and hafnium ions; (B) (i) chlorinating zircon sand in the presence of carbon, such as coke, at about 800° C. to 1200° C. to produce a crude $ZrCl_4/HfCl_4$ fraction and a $SiCl_4$ fraction; (ii) selectively isolating the $ZrCl_4/HfCl_4$ fraction from the $SiCl_4$ fraction; and, (iii) hydrolyzing the crude $ZrCl_4/HfCl_4$ fraction with ice ($H_2O_{(s)}$), preferably in the form of crushed ice, at a temperature of about 0° C. to 10° C. to form the feedstock solution of zirconium and hafnium ions; or, (C) (i) chlorinating zircon sand in the presence of carbon, such as coke, at about 800° C. to 1200° C. to produce a crude $ZrCl_4/HfCl_4$ fraction and a $SiCl_4$ fraction; (ii) selectively isolating the $ZrCl_4/HfCl_4$ fraction from the $SiCl_4$ fraction; (iii) subliming the $ZrCl_4/HfCl_4$ fraction at a temperature of about 200° C. to 450° C. and a pressure of about 5 to 25 psi to form a $ZrCl_4/HfCl_4$ vapor fraction; (iv) partially hydrolyzing the $ZrCl_4/HfCl_4$ vapor fraction with steam ($H_2O_{(g)}$) to from a $ZrOCl_2/HfOCl_2$ vapor fraction and an HCl vapor fraction; (v) removing the HCl vapor fraction for reuse; (vi) condensing the $ZrOCl_2/HfOCl_2$ vapor fraction to an anhydrous $ZrOCl_2/HfOCl_2$ aqueous fraction; and, (vii) completely dissolving the $ZrOCl_2/HfOCl_2$ fraction in water or aqueous acid, such as HCl, to form the feedstock solution of zirconium and hafnium ions.

4. BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the spirit and scope of the appended claims. In the drawings.

5. DETAILED DESCRIPTION OF THE PREFERRED EMBODIMENTS OF THE INVENTION

The invention provides both the processing method and system for the continuous, steady-state, separation and purification of the elements zirconium (Zr) and hafnium (Hf) from crude zirconium minerals containing hafnium impurities in a single procedure preferably in a continuous annular chromatograph (CAC) device, which does not substantially generate inseparable complexes of zirconium and hafnium as a by-product, and which also improves separation kinetics, and reduces amounts of waste generation. The resultant separated and purified zirconium and hafnium products from the method and system of the invention can then be used as nuclear grade zirconium and hafnium materials of construction for nuclear reactors. The resultant separated and purified zirconium and hafnium products can also be used, if desired, to support further separation processing into their individual isotopes, either performed concurrently in the same procedure or subsequently in another operation, to provide isotopically enriched nuclear grade zirconium and hafnium materials of construction for nuclear reactors.

The earlier mentioned U.S. patents, namely U.S. Pat. Nos. 5,023,061; 5,024,749; 5,098,676; 5,110,566; 5,112,493; and, 5,174,971, teach technically feasible techniques and equipment for chromatographically separating zirconium from hafnium using a continuous annular chromatograph (CAC) in a single, continuous, steady-state, operation, all of these disclosures being incorporated by reference herein in their entireties. The primary focus of these references, however, was the chromatographic operation itself with only passing attention being paid to the feedstock pretreatment and optimization techniques. Despite the technical and economic success of this art, the chromatographic separation processes for zirconium and hafnium separations require more detailed attention to feedstock solution preparations in order to achieve process optimization, cost reduction, waste reduction and systematic, reproducible and reliable operations for producing nuclear quality materials.

In these earlier efforts of chromatographic processing in a CAC, the inventors attempted to use pure, as well as mixed, chloride-based systems by generally: (A) feeding aqueous crude zirconium chloride feedstock solution of dissolved and dissociated $ZrOCl_2$ (which also contained $HfOCl_2$) derived from the aqueous hydrolysis of a carbochlorination product of crude zircon sand; (B) feeding chloride eluant solutions of HCl or $HClO_4$, as well as non-chloride eluant solutions of $H_2SO_4$, $H_3PO_4$ or $HNO_3$, to the CAC to elute the feedstock solutions from the ion exchange resin; and, (C) recovering the separated and purified zirconium and hafnium product fractions and waste products from the CAC for further processing into their respective metals. However, as described above, these prior methods were accompanied by the production of inseparable zirconium and hafnium co-polymer complexes as by-products of the separation processes, which reduced the overall quality of the resultant nuclear grade materials. Once formed, the inseparable complexes tended to contaminate the zirconium product wave front exiting the CAC which consequently diminished the overall quality of the resultant nuclear grade material as well as its yield.

In further detail, the prior methods for preparing the crude aqueous chloride feedstock solutions of zirconium and hafnium ions of step (A) which have been found to have drawbacks but which have been used to support continuous, steady-state, ion exchange chromatographic separations of zirconium from hafnium in a CAC were by: (i) halogenating, e.g., chlorinating, crude zirconium minerals, for instance, crude zircon ($ZrSiO_4$), which typically contain a natural distribution of zirconium isotopes and also 1 to 5% hafnium contamination as well as other transition metal and radio-chemical impurities, in the presence of a carbon source, e.g., petroleum coke, at temperatures of about 800° C. to 1200°, typically about 1000° (otherwise known as the carbochlorination of crude zirconium minerals); (ii) separating the resultant crude zirconium tetrachloride ($ZrCl_4$) fraction which also contains hafnium tetrachloride ($HfCl_4$) from the resultant silicon tetrachloride fraction ($SiCl_4$), typically in a differential condenser; (iii) partially hydrolyzing with water the separated $ZrCl_4/HfCl_4$ fraction by beginning at a starting solution temperature of about 25° C. (but as the hydrolysis reaction proceeds, the hydrolysis reaction exotherm drives the solution temperature up to about 100° C. or greater along with the acid generation rate, thereby causing cross-polymerization side reactions) to yield an aqueous solution of zirconium oxychloride ($ZrOCl_2$) which also contains hafnium oxychloride ($HfOCl_2$) and excess free acid hydrogen ions and HCl in solution; (iv) separating the HCl by-product, typically in an HCl absorber; and, (v) completely dissolving the $ZrOCl_2/HfOCl_2$ fraction in water or aqueous acid solution to yield the aqueous ionic chloride feedstock solution. In the feedstock solutions, a lower acid concentration tends to form zirconium cations, whereas a higher acid concentration tends to form zirconium anions. Alternatively, the crude $ZrCl_4/HfCl_4$ could be dissolved directly in a single step, however, the absence of HCl in the two-step process increases the solubility of zirconium in water, to allow the production of higher feedstock zirconium concentrations. These conventional crude feedstock solutions are then injected into the ion exchange column of the CAC with eluant solutions to support the separation and purification of zirconium from hafnium at room temperature.

Historically, therefore, in order to form the chloride feedstock solutions of ionic compounds of crude zirconium which also contains crude hafnium, the zirconium tetrachloride and hafnium tetrachloride fraction from the carbochlorination of the crude zirconium minerals are hydrolyzed starting at room temperature (approx. 25° C.), but once the hydrolysis reaction begins, the hydrolysis exotherm drives the solution temperatures up to about 100° C. or greater along with the free acid ($H^+$) generation rate, to yield an aqueous ionic solution which also contains inseparable zirconium and hafnium co-polymers, and which consequently are lost for use as a feedstock for the separation process. The usable as well as the unusable co-polymerized portions of the feedstock solutions are then conventionally fed typically at room temperature (approx. 25° C.) to a continuous, steady-state, ion exchange chromatographic column containing cationic or anionic ion exchange resins, preferably in a continuous annular chromatograph (CAC) also typically operating at room temperature (approx. 25° C.), along with an aqueous acid eluant solution for elution of the separated zirconium and hafnium fractions into distinct product streams for isolation.

However, the inventors have discovered that by using these conventional methods, as generally taught in the earlier U.S. patents hereinabove, the separated nuclear grade zirconium product fraction purity is marred by incomplete separation and inclusion of hafnium with the zirconium which undesirably alters the thermal neutron absorbing properties of the nuclear grade zirconium. This has led the inventors to study the feedstock preparation methods and chemical and thermodynamic mechanisms therefore, since the generation of substantially pure hafnium-free zirconium is extremely desirable for ultimate use as a nuclear grade material or if desired for use as a feedstock to support further zirconium isotope separation.

The method and system of the invention provide for the continuous, steady-state, ion exchange chromatographic separation of zirconium from hafnium and optionally isotopes thereof, in a CAC using pure chloride-based systems, while simultaneously inhibiting the production of inseparable zirconium and hafnium co-polymer complexes, thereby improving the quality of the resultant nuclear grade material. The improvements can be realized in one instance by controlling the exotherm and free acid generation typically associated with the preparation of conventional crude zirconium oxychloride ($ZrOCl_2$) also containing hafnium oxychloride ($HfOCl_2$) feedstock solutions. The improvements can be realized in another instance by reducing the chromatographic processing temperatures. These, in turn, reduce or eliminate the cross-polymerization side reactions of zirconium and hafnium.

The method and the system of the present invention particularly improves continuous, steady-state, ion exchange chromatographic separation of (1.) elemental zirconium and hafnium and/or (2.) isotopes thereof from the hydrolyzed crude carbochlorination products of zircon or other zirconium minerals by using chloride chemistry for the separations, by improving the crude zirconium feedstock solution preparation conditions to inhibit the formation of zirconium and hafnium co-polymers during hydrolysis and also during chromatographic processing, and also by improving other chromatographic processing conditions to improve the separation kinetics, which results overall in improved separations of zirconium and hafnium with reduced waste generation and reduced operating costs over prior methods and systems. The method and system of the invention is preferably used to generate substantially hafnium-free nuclear grade zirconium for nuclear applications and also used to generate substantially hafnium-free zirconium feedstocks to support zirconium isotope separation to generate substantially hafnium-free isotopically enriched nuclear grade zirconium.

In their studies, the inventors have discovered that the aqueous hydrolysis reactions of crude zirconium tetrachloride and also hafnium tetrachloride to yield a separable feedstock solution of ions, e.g., $ZrO^{+2}$ and $HfO^{+2}$ (cations) or $ZrOCl_4^{2-}$ and $HfOCl_4^{2-}$ (anions), etc., are slow to come to equilibrium and produce exotherms, i.e., a rise and fall in temperature of the reactive system over the reaction time. As a consequence, some of the zirconium and hafnium compounds in aqueous solution are cross-polymerized to yield inseparable zirconium and hafnium complexes which are not amenable to ion exchange chromatographic separations, thereby resulting in incomplete separation and hafnium contamination in the zirconium fractionated product. Moreover, the inventors have discovered that in addition to the hydrolysis exotherm, the presence of free hydrogen ions ($H^+$) or free acids generated during the aqueous hydrolysis reactions tend to accelerate and catalyze the cross polymerization of zirconium and hafnium and also tend to cause premature elution (or leakage) of the zirconium or hafnium fractions once loaded in the continuous ion exchange chromatograph column. The generation of free acid is also increased as the exotherm increases the temperature of the hydrolysis solution.

The hydrolysis reactions of the crude zirconium and hafnium carbochlorination products to produce a feedstock solution of ions to load to the ion exchange chromatographic separation column are believed to be represented by Equations (1) and (2), and the cross-polymerization reaction of the resultant oxychlorides of Equations (1) and (2) is believed to be conceptually represented by Equation (3).

(1)

(2)

(3)

The dissolution, i.e., dissociation, reaction can be represented by Equation (4).

(4)

The cross polymerization side reaction represented by Equation (3) is undesirable but readily occurs in conventional the feedstock preparations of ionic aqueous chloride solutions of zirconium (also containing hafnium) used to support continuous ion exchange chromatographic separation technique for the separation of zirconium from hafnium and/or of isotopes thereof. Whereas, the method and system of the invention substantially reduces or eliminates cross-polymerization side reaction and the formation of inseparable zirconium and hafnium co-polymer complexes in solution, prior to and during continuous ion exchange chromatographic separation operations, especially when performed in a continuous annular chromatograph (CAC) and in a single operation.

Figure 1:
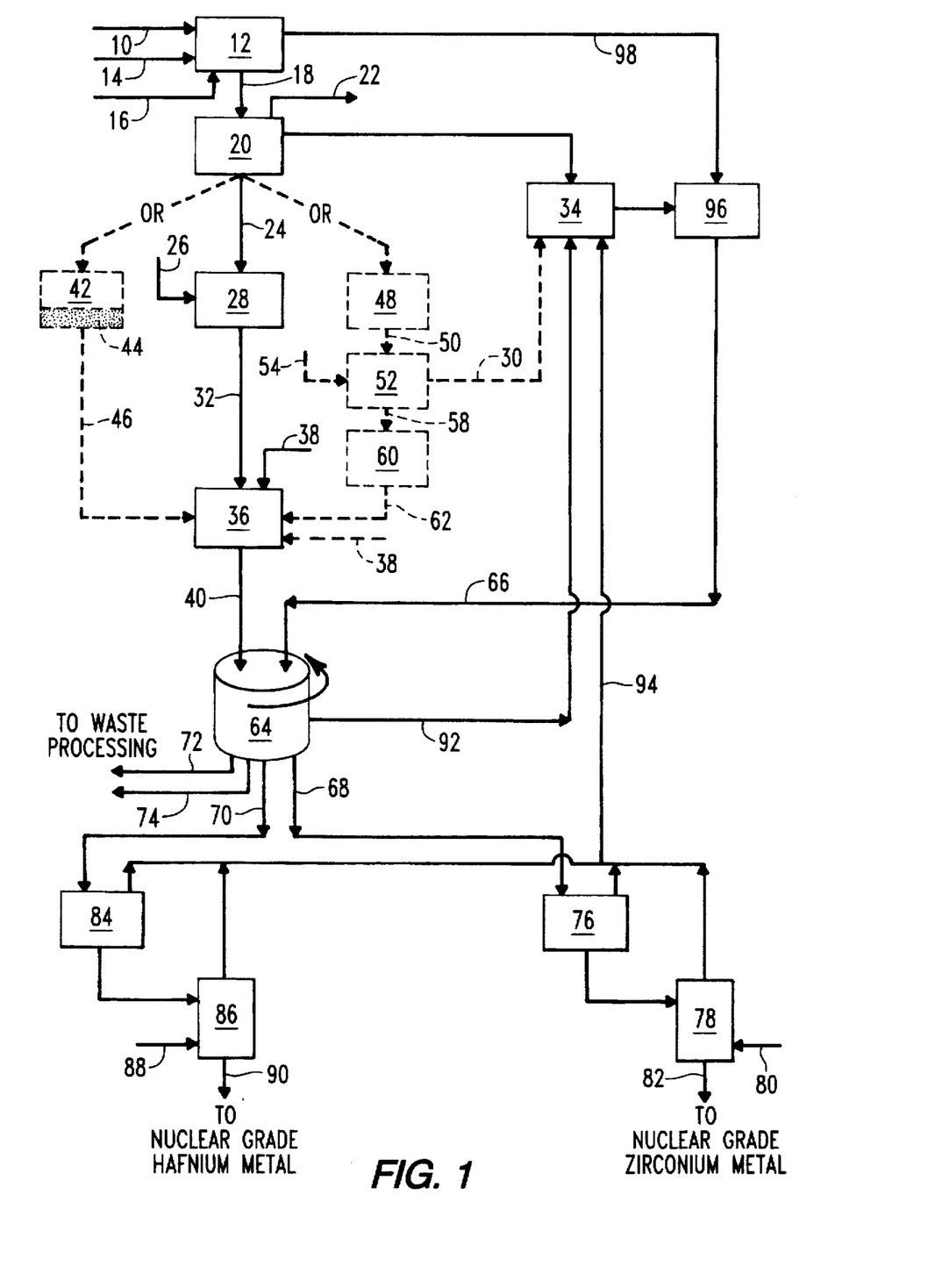
FIG. 1 is a schematic flow diagram of the zirconium and hafnium separation method and system of the invention.

Referring now to the drawings, FIG. 1 is a schematic flow diagram of the method and system of the present invention for the separation of zirconium from hafnium with substantial elimination of the cross-polymerization reaction of zirconium and hafnium which forms generally inseparable Zr-Hf co-polymerized by-products. As shown, crude zircon sand (10) ($ZrSiO_4$) which also contains hafnium, typically about 1 to 5% hafnium, is fed to a chlorinator (12) and chlorinated to yield zirconium tetrachloride ($ZrCl_4$) and also hafnium tetrachloride ($HfCl_4$) fraction and silicon tetrachloride ($SiCl_4$) fraction in the presence of a carbon source (14), preferably coke, and chlorine ($Cl_2$) gas (16) at a temperature in the range of about 800° C. to 1100° C. A carbon:zircon sand ratio of about 21:79 parts is preferred. A gaseous stream (18) exits the chlorinator (12) containing both the $ZrCl_4$/$HfCl_4$ and $SiCl_4$ fractions and is selectively condensed in a condenser (20). The selective condensation produces two streams, $SiCl_4$ by-product fraction (22) and a crude $ZrCl_4$/$HfCl_4$ fraction (24). The combined $ZrCl_4$/$HfCl_4$ product fraction (24) is processed further to form a crude zirconium chloride-based feedstock solution which is ultimately chromatographically processed and separated into zirconium and hafnium metals, and also optionally further separated into zirconium isotopes and hafnium isotopes, to produce high quality nuclear grade materials.

In the present invention, the hydrolysis of the crude carbochlorinated $ZrCl_4$/$HfCl_4$ fraction (24), according to the hydrolysis reactions as represented by Equations (1) and (2) above, is carefully controlled to substantially reduce the formation of inseparable zirconium and hafnium co-polymer complexes as represented by Equation (3). The exotherms produced during the hydrolysis reactions along with the free acid ($H^+$) hydrolysis by-product tend to drive the cross-polymerization of the oxychlorides of zirconium and hafnium produced during hydrolysis. The crude $ZrCl_4$/$HfCl_4$ fraction (24) is, therefore, hydrolyzed under controlled conditions which either eliminate the hydrolysis exotherm and/or eliminate the hydrolysis free acid ($H^+$) by-product, thereby, in both cases, preventing or inhibiting cross-polymerization of hafnium and zirconium into inseparable complexes, and in the latter case also preventing premature elution in the separation column.

In a first alternative processing method of the invention that is used to produce the crude aqueous zirconium complexed chloride feedstock solutions to support the continuous ion exchange chromatographic separation of zirconium from hafnium, the crude $ZrCl_4/HfCl_4$ fraction (24) is hydrolyzed with controlled cooling in a two-step aqueous phase method to substantially eliminates both the hydrolysis exotherm and the catalytically effective free acid ($H^+$) which both tend to drive the cross polymerization reaction of the zirconium-hafnium oxychloride hydrolysate. While previous attempts were made to use a two-step hydrolysis process as described particularly in U.S. Pat. No. 5,112,493 (Snyder, et al.) which targets the reduction of free acid to improve the zirconium solubility, a chilled dissolution was neither contemplated nor suggested, since it was desirable to drive up the temperature of the feedstock solutions during the hydrolysis operation in order to use a hot feedstock solution during chromatographic processing to further improve the solubility of the zirconium and not allow crystallization of the zirconium out of the feedstock solution. The inventors, however, surprisingly and unexpectedly discovered now that controlling the temperature is the dominant variable in obtaining desirable feedstock solutions for chromatographic processing and improving the chromatographic separations.

In the first step of this embodiment, excess $ZrCl_4/HfCl_4$ fraction (24) is directed in the presence of starved amounts of water ($H_2O_{(l)}$) (26) to a hydrolysis reactor (28), such as a turbulizer. The hydrolysis reactor (28) is preferably operated at a controlled low temperature of about 0° C. to 110° C., more preferably about 10° C. to 25° C., to remove the heat generated during the exothermic hydrolysis reaction. Cooling of the hydrolysis reactor (28) can be performed either through an external refrigeration jacket (not shown) or the injection of contact refrigerants (not shown), such as super-cooled water, $CO_2$ (cooled gas or liquid), $N_2$ or $O_2$. The lowering of the temperature and continual removal of heat substantially eliminates the hydrolysis exotherm which tends to drive the cross-polymerization reaction and production of zirconium and hafnium co-polymers.

In the first partial hydrolysis step, a hydrochloric acid (HCl) stream (30) by-product is driven off and a crude zirconium oxychloride ($ZrOCl_2$) which also contains hafnium oxychloride ($HfOCl_2$) (otherwise $ZrOCl_2/HfOCl_2$) fraction (32) is provided. The HCl by-product stream (30), which is anhydrous HCl, is directed to an HCl absorber (34) and can be stored for reuse in the invention such as for use as the eluant solution. The absence of HCl also increases the solubility of zirconium in water, thereby allowing for higher zirconium concentrations in the feedstock solution.

In the second step of this first alternative embodiment, the partially hydrolyzed crude $ZrOCl_2/HfOCl_2$ stream (32), which is anhydrous $ZrOCl_2/HfOCl_2$, is directed to a feedstock solution tank (36), where substantially complete dissolution and dissociation of the crude $ZrOCl_2/HfOCl_2$ fraction (32) in the presence of water (38) or aqueous acid, such as HCl, occurs. The acid strength during dissolution dictates whether a solution of zirconium cations or zirconium anions is produced. Zero or low acid concentrations typically produce solutions of $ZrO^{+2}$ and $HfO^{+2}$ cations, whereas high acid concentrations typically produce solutions of $ZrOCl_4^{-2}$ and $HfOCl_4^{-2}$ anions. The feedstock solution tank (36) is preferably operated at controlled temperature of about 0° C. to 110° C., more preferably about 10° C. to 25° C., to yield an aqueous chloride feedstock solution (40) of ionic compounds of zirconium and hafnium ions which is suitable for use as the feed phase for a continuously operating, steady-state, ion exchange chromatographic separation column such as a CAC device. Cooling of the feedstock solution tank (36) can be performed either through an external refrigeration jacket (not shown) or the injection of contact refrigerants (not shown), such as super-cooled water, $CO_2$ (cooled gas or liquid), $N_2$ or $O_2$. The lowering of the temperature of the feedstock solution tank (36) and continual removal of heat substantially eliminates any hydrolysis exotherm and also can provide a cooled aqueous chloride feedstock solution to the chromatographic column to improve the separation kinetics.

The aqueous chloride-based feedstock solution (40) is accordingly provided with substantial elimination of the formation of zirconium and hafnium co-polymers. This results from removing the hydrolysis exotherm and HCl prior to complete dissolution to substantially eliminate the presence of heat and free acid ($H^+$) generated by the hydrolysis reactions which catalyze and accelerate the cross polymerization reaction. The absence of HCl also increases the solubility of zirconium in water.

In a second alternative method (as shown by dotted lines to the left of the first alternative method in FIG. 1), the crude $ZrCl_4/HfCl_4$ fraction (24) is hydrolyzed and dissolved with cooling in a one-step direct aqueous phase hydrolysis process to substantially eliminate the hydrolysis exotherm which tends to drive the cross-polymerization reaction. This second alternative method is the preferred method for the feedstock preparation. In this direct hydrolysis alternative embodiment, the crude $ZrCl_4/HfCl_4$ fraction (24) is directed to a hydrolysis reactor (42) in the presence of water (44) ($H_2O_{(s)}$) in the form of crushed ice at a temperature of about 0° C. to 5° C., preferably about slightly above 0° C. The crushed ice (44) is, therefore, used as the hydrolysis reagent. The hydrolysis reactor (42) can also be further cooled to maintain a temperature of about 0° C. to 10° C., preferably 0° C. to 5° C., by either an external refrigeration jacket (not shown) or by the injection of contact refrigerants, e.g., super-cooled $H_2O$, $CO_2$ (cooled gas or liquid), $N_2$ or $O_2$. Further, in this second alternative embodiment, an ionic aqueous chloride-based feedstock solution (46) of zirconium and hafnium ions are produced at a reduced temperature to substantially eliminate the hydrolysis exotherm. The feedstock solution (46) is then directed to a feedstock solution tank (36) which holds the crude aqueous chloride feedstock solution (40) used to support chromatographic processing. The feedstock solution (40) can also be combined with aqueous acid such as HCl. This embodiment is more desirable since although free acid ($H^+$) is present in the ion exchange chromatographic feedstock solution (40) which can have catalytic effects on the cross-polymerization of zirconium and hafnium in the separation column, the temperature impact on the cross-polymerization reactions is found to dominate.

In a third alternative method (as shown in dotted lines to the right of the first alternative method in FIG. 1), the crude $ZrCl_4/HfCl_4$ fraction (24) is hydrolyzed with steam (water vapor) in a two-step vapor phase method to substantially eliminate the free acid ($H^+$) catalyst which tends to catalyze the cross polymerization reaction of the zirconium-hafnium oxychloride hydrolysate, and which also tends to cause premature elution of the zirconium or hafnium product fraction in the separation column. In the first step of this third alternative embodiment, the $ZrCl_4/HfCl_4$ (24) is directed to a sublimation reactor (48) where it is caused to sublime to its vapor phase at a temperature of about 300° C.

to 500° C., preferably about 330° C. to 450° C., and a reactor pressure of about 5 to 35 psi, preferably 10 to 20 psi. Thereafter, the $ZrCl_4/HfCl_4$ vapor (50) is directed to a hydrolysis reactor (52) where it is partially hydrolyzed in the presence of water vapor (steam) (54) at a temperature of about 100° C. to 300° C., preferably about 100° C. to 200° C., and a pressure of about 5 to 35 psi, preferably about 10 to 20 psi. An HCl by-product stream (30) is driven off and a crude $ZrOCl_2/HfOCl_2$ gas fraction (58) is cooled and condensed in a condenser (60) to anhydrous $ZrOCl_2/HfOCl_2$ fraction (62). The $ZrOCl_2/HfOCl_2$ fraction (62) is then directed to a feedstock solution tank (36) where substantially complete dissolution of the crude $ZrOCl_2/HfOCl_2$ fraction is achieved in the presence of water (38) or aqueous acid such as HCl, to yield a crude aqueous chloride-based feedstock solution (40) of zirconium and hafnium ions used to support chromatographic processing. This embodiment substantially eliminates the presence of free acid ($H^+$) which tends to catalyze the Zr-Hf cross-polymerization reactions and also tends to cause premature elution of the Zr or Hf product fractions in the separation column. Also, since the molecules of $ZrCl_4$ and $HfCl_4$ are hydrolyzed in the vapor phase, they are far less likely to cross-polymerize during hydrolysis. Accordingly, only weak physical association bonds are formed during condensation which are easily broken during dissolution and chromatographic processing.

The crude zirconium-hafnium hydrolysate chloride feedstock solution (40) prepared by either of these three alternative methods, which all inhibit the formation of zirconium and hafnium co-polymers, is fed to a continuously and steady-state operating ion exchange chromatographic separation column (64), preferably a continuous annular chromatograph (CAC) device. An aqueous eluant solution stream (66), which is preferably an aqueous acid solution, most preferably HCl, as will be described in detail hereinbelow, is directed to the CAC device (64). The zirconium-hafnium feedstock solution (40) is separated therein into distinct zirconium product fractions (68) and hafnium product fractions (70) which are also separated and purified of other metal contaminants, specifically, heavy and transition metal wastes (72) and radioactive metal wastes (74). Typically, the transition metal contaminants such as Al, Fe, etc., which occur cationically in the feedstock solution, and the radiochemical contaminants such as the actinides, which occur anionically in the feedstock solution, will generate two separate waste fractions, thereby decreasing the waste volume and eliminating the formation of mixed wastes for further processing. The heavy and transition metals typically do not form complexes which interact with the ion exchange resins as strongly as the zirconium and hafnium complexes consequently wash through the chromatographic column, while the radiochemical contaminants do complex somewhat with the exchange resins and need to be eluted off the chromatographic column.

The aqueous zirconium product fraction (68) is the directed first to a zirconium concentrator (76) where it is evaporated and then to a spray roaster (78), which is preferably heated by a gas burner (80). The zirconium product fraction (68) is spray roasted to a substantially pure zirconium oxide ($ZrO_2$) product (78). The $ZrO_2$ (78) is then chlorinated (not shown in the process schematic of FIG. 1) and subsequently reduced to nuclear grade zirconium metal.

The aqueous hafnium product fraction (70) is subjected to the same processing as the zirconium fraction (68). The aqueous hafnium fraction is first concentrated in a concentrator (84) and then spray roasted in a spray roaster (86), which is preferably heated by a gas burner (88), to produce a substantially pure hafnium oxide ($HfO_2$) product (90). The $HfO_2$ product (90) is then chlorinated (not shown in the process schematic of FIG. 1) and subsequently reduced to nuclear grade hafnium metal.

The aqueous zirconium product fraction (68) and the aqueous hafnium product fraction (70) prior to product recovery steps can be further used if desired as feedstock solutions to support isotopic chromatographic processing in either the same or separate operation. An inherent result of a resolution of the isotopes of a zirconium is an efficient separation of hafnium from zirconium. Another inherent result of this isotopic resolution is the efficient separation of the heavy and transition metal contaminants and radiochemical contaminants from not only the zirconium and hafnium but also from each other.

The aqueous heavy and transition metal waste fraction (72) and the aqueous radiochemical waste fraction (74) are subjected to volume reduction (not shown in the process schematic of FIG. 1) and can be disposed of as dry solids. The disposal of these waste materials as solids is substantially easier than their disposal as aqueous or organic liquids. Moreover, they are inherently separated from each other by the chromatograph so additional processing to separate the heavy and transition metal wastes and radiochemical wastes is not required, thus making the disposal of these two classes of wastes less burdensome. This capability provides an additional waste management benefit.

The acid eluant (66) can be recycled in a recycle line (92) after it has been passed through the CAC (64). This acid eluant is recycled through an acid absorber such as the HCl absorber (34). In addition, acid, typically HCl, from the zirconium concentrator (76) and spray roaster (78) and the hafnium concentrator (84) and spray roaster 86 is directed along acid recycle line (94) to the HCl absorber (34). The HCl acid eluant is stored in an acid feed storage tank (96) from which it is pumped back to the continuous annular chromatograph (64) along an eluant supply line (66). Some acid is typically generated by the present process, usually in the form of HCl. Some of the chlorine supplied to the chlorinator (12) will react with the zircon sand and coke to form the $SiCl_4$ by-product (22). The remainder of the $Cl_2$ forms hydrochloric acid (98) which may be combined with the acid eluant and used in the chromatographic separation. Since all barren acid eluant streams are recycled directly to the chromatograph, there are no aqueous wastes to be discharged.

It is preferred that the feed phase (40), i.e., the crude aqueous chloride feedstock solution of zirconium and hafnium ions, have a concentration of crude zirconium and hafnium as high as is compatible with the solubility under the anticipated operating conditions, i.e., close to the solubility limit. The natural consequence of ion exchange chromatographic separation is a dilution of the concentration of the products being separated into distinct product fractions. Therefore, the overall efficiency of the process and particularly a minimization of the efforts needed to recover the desired product fraction is best served by using as high a concentration as possible in the feedstock solution without creating an undue risk that zirconium will precipitate out during the separation process. It is preferred to use a zirconium concentration in the feed phase of about 50–200 g/l, preferably about 130 to 140 g/l. The solubility of zirconium at 25° C. in water is about 130 g/l or greater and in 25 w/o HCl is about 20 g/l or less. The zirconium solubility, however, drops steeply with increasing HCl concentrations, and ranges from about 200 g/l at 2N HCl to 10 g/l a 6N HCl at 25° C. Accordingly, lesser amounts of HCl provide for higher concentrations of zirconium in the feedstock solutions.

It is preferred to effect elemental Zr and Hf separations in at least one first chromatographic column using the aqueous chloride feedstock solutions of zirconium and hafnium ions as described above and, if desired, then effect isotopic separations in at least one subsequent chromatographic column using a refined aqueous feedstock solution obtained from the first column.

It is preferred that the mobile phase or eluant be any aqueous acid solution capable of solvating the zirconium ions such that they can be eluted down the column. This mobile phase or eluant is a fluid capable of displacing the zirconium ions from their ionic association with the stationary phase. It is preferred to use aqueous chloride solutions as the eluant, since chloride feedstock solutions mixed with other acid chemistries can result in additional waste generation and additional processing to separate the mixed chloride and other acids for recycle. It is most preferred to use an aqueous solution of hydrochloric acid (HCl) although other acids such as perchloric acid ($HClO_4$), sulfuric acid ($H_2SO_4$), nitric acid ($HNO_3$) or the like may also be used. The drawbacks of using mixed chloride feedstock solutions, and sulfate eluant solutions, are further explored in co-pending U.S. patent application Ser. No. 08/502,995 filed on Jul. 17, 1995, now U.S. Pat. No. 5,618,502, of inventors C. H. Byers, W. G. Sisson, T. S. Snyder, R. J. Beleski, T. L. Francis, and U. P. Nayak, which is entitled *Zirconium and Hafnium Separation In Sulfate Solutions Using Continuous Ion Exchange Chromatography*, the disclosure being incorporated by reference herein in its entirety.

The acid strength of the eluant needed is dependent on the nature of the ions, either cations or anions. Since the zirconium solubility drops very steeply with increasing HCl concentrations, eluant concentrations should be from about 2N to 4.5N HCl, more preferably from about 2.5N to 3.0N HCl. Eluant concentrations greater than about 4.5N HCl are not especially preferred due to the low solubility of zirconium. Also, eluant concentrations less than about 2.0N HCl are not especially preferred due to high retention time in the chromatographic column as well as high product dilution with eluant in order to elute the product from the column, which both increase product recovery costs. The precise acid strength needed, however, will depend upon the nature of the active groups of the stationary phase and the eluant acid species. It is also possible to use water as the eluant, since it will form a more dilute solution of the feed phase as it passes down the column.

The preference for a hydrochloric acid (HCl) eluant is based on both its advantageous chemical and transport interactions with hafnium and zirconium and its compatibility with the crude aqueous chloride feedstock solutions of zirconium and hafnium ions which reduces waste generation. The separation of zirconium from hafnium and the separation of the isotopes thereof is particularly efficient with HCl as the eluant, indicating that it promotes an optimum balance of affinity to and release from the stationary phase ion exchange resin beads. Since the feedstock is obtained by chlorinating zircon sand and hydrolyzing the resultant tetrachlorides into oxychlorides, they are, of course, highly compatible with hydrochloric acid. The mobile phase can also include other additives such as crown ethers, chelants, and the like which can amplify the elution mechanism. The mobile phase is also preferably recycled and purified for reuse.

Also, according to the feedstock preparation scheme as fully described hereinabove, the removal of the excess ($H^+$) free acid ion during the feed preparation hydrolysis reactions advantageously allows the feedstock solution of ions to load in the continuously operating ion exchange chromatographic column without premature elution (or leakage) of the zirconium or hafnium fractions due to the presence of free acid in the feedstock solution.

It is preferred that stationary phase be any cationic ion exchange resin with an affinity for zirconium cations in the feedstock solution, typically in the form of $ZrO^{2+}$ and $HfO^{2+}$ or the like. It is preferred that the cationic exchange resin be capable of displaying a very strong affinity for zirconium cations. Preferred cationic exchange resins can be based on active groups of carboxylic, sulfonic, phosphonic acids, in the hydrogen form, or the like and include weak and strong acid resins, for example, Dowex 50W-X8 resin sold by Dow Chemical Corporation, or the like. The stationary phase can also be any anionic ion exchange resin with an affinity for zirconium anions in the feedstock solution, typically in the form of $ZrOCl_4^{2-}$ and $HfOCl_4^{2-}$ or the like. Preferred anionic exchange resins can be based on active groups of quaternary ammonium or amino groups or the like, in the chloride form, and include weak and strong base resins. The use of anionic exchange resin tends to enhance the separation since in this case chloride ions, not hydrogen ions, are the eluant species. Reference can be made to *Perry's Chemical Engineers Handbook*, McGraw Hill Publishing Co., NY, N.Y., 6th edition (1984), pp. 16-1 to 16-48 including Table 16-4 for a description of cationic and anionic exchange resins suitable for use in the method and system of the invention, this disclosure being hereby incorporated by reference herein.

It is also preferred that the stationary phase have a monodisperse distribution of spherical particles with an average particle size of less than about 10 microns, preferably less that about 1 micron. It is further preferred that the stationary phase have a high ionic capacity per unit volume, preferably between about 0.01 to 0.5 milliequivalents per milliliter.

The effective column height should be sufficient to allow significant resolution of the hafnium and zirconium into distinct product fractions. If desired, the effective column height may be increased to allow significant resolution of various isotopes of the element of interest, zirconium or hafnium, into distinct product fractions. The resolution is preferably sufficient to yield an element or isotope purity at least of about 50%, preferably in excess of about 90%, more preferably at least about 98%. It is preferred to have zirconium product concentration greater than about 10 g/l, preferably greater than about 15 g/l, more preferably between about 20 to 190 g/l exiting the chromatographic column in the zirconium product fraction. It is further preferred to attain a product purity of less than 100 ppm hafnium in the zirconium product fraction, preferably less than 50 ppm. It is preferred that this resolution be effected in a single pass through the column. The effective column height needed for a given resolution can be estimated from an application of the Kremser-Brown Saunders equation, to empirical data on the separation capacity of a given feedstock, ion exchange resin, eluant, and flow conditions.

A theoretical separation factor alpha, $\alpha_r$, is used to define the ability to separate the various elements and isotopes. This factor $\alpha_r$ is itself defined by the following formula for the binary case:

$$\alpha_r = (y/(1-y))/(x/(1-x))$$

where y is the molar concentration of the desired element or isotope in the product rich fraction ("heads") in that element or isotope, and x is the molar concentration of the same element or isotope in the product poor fraction ("tails") in that element or isotope. Theoretical stage separation factors, $\alpha_s$, are conveniently evaluated on 25 to 100 cm test columns, with a 25 cm column being preferred. The preferred feedstocks, eluants, ion exchange resins and conditions should have a separation factor of about 1.001 to 1.5, preferably about 1.03 to 1.10. The effective column length for the desired separation is then determined by estimating the number of theoretical stages, N, required of 25 cm each in length by the following formula:

$$N = \ln \alpha / \ln \alpha_s.$$

The effective column height can be vertical but it can also have other orientations. What is important is the effective path over which the mobile phase travels. It is preferred that the path be provided in such a way that the chromatographic separation can be operated continuously. Presently, there is no convenient technique available for instantaneously sensing the concentration of the product fractions. Thus, there is a preference for a continuously operating method which has reached steady-state so that a particular product fraction reproducibly has a certain product distribution. If the ion exchange chromatographic separation is effected in a discontinuous or batch manner, random variations between runs may make it difficult to reproducibly collect product fractions with the same product distribution from run to run. For instance, if a single vertical column is loaded in a batch manner the elution time of the product fraction rich is a particular product may vary from run to run due to random variables difficult to control such as feedstock concentration fluctuations, etc.

It is further preferred according to the method and system of the invention to optimize the separation kinetics through control of the feedstock solution, eluant solution and/or chromatographic column temperature during ion exchange chromatographic operations. As shown in Table 2, zirconium and hafnium separation kinetics are temperature dependent with a maximum separation factor alpha obtained between about 0° C. and 5° C. Thus by controlling the column temperature, and/or the feedstock and eluant solution temperatures, the present invention tends to optimize the separation of zirconium from hafnium. Moreover, controlling the column temperature will tend to reduce any cross-polymerization of the zirconium and hafnium which may also occur in the separation column during ion exchange chromatographic operations.

TABLE 2

Zirconium and Hafnium Separation Kinetics on Dowex 50W-X8 Cationic Exchange Resin

| Run Temp. (°C.) | Alpha ($K_{Hf}/K_{Zr}$) |
| --- | --- |
| 25 | 3.16 |
| 15 | 3.10 |
| 4.5 | 4.38 |
| 0 | 5.65 |
| −5.3 | 5.32 |

Figure 2:
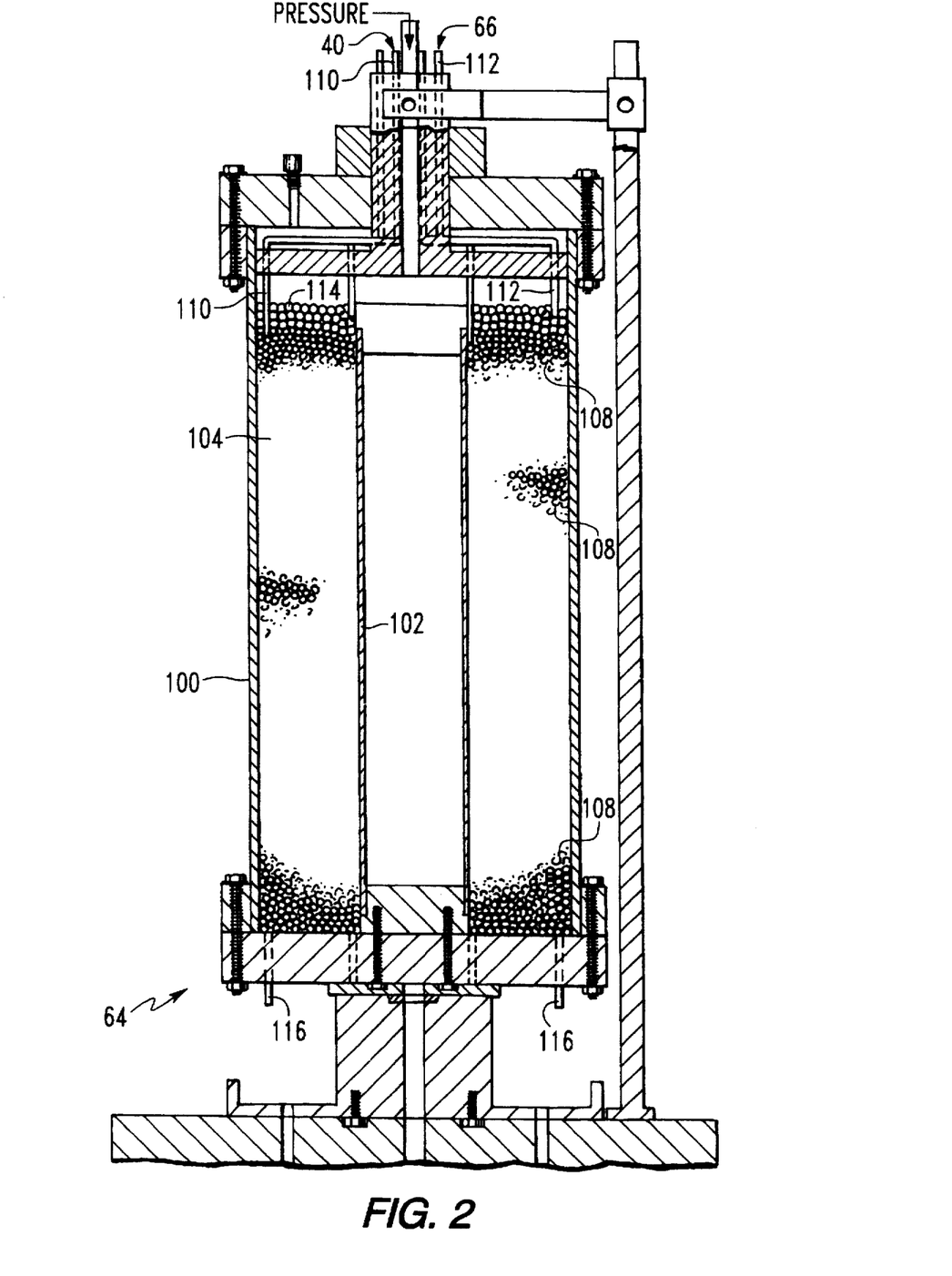
FIG. 2 is a vertical sectional view of a continuous annular chromatograph device used in the zirconium and hafnium separation method and system of the invention; and, FIG. 3 is a perspective view of a continuous annular chromatograph device with a portion in section to show the annular chromatographic separation column used in the zirconium and hafnium separation method and system of the invention.
Figure 3:
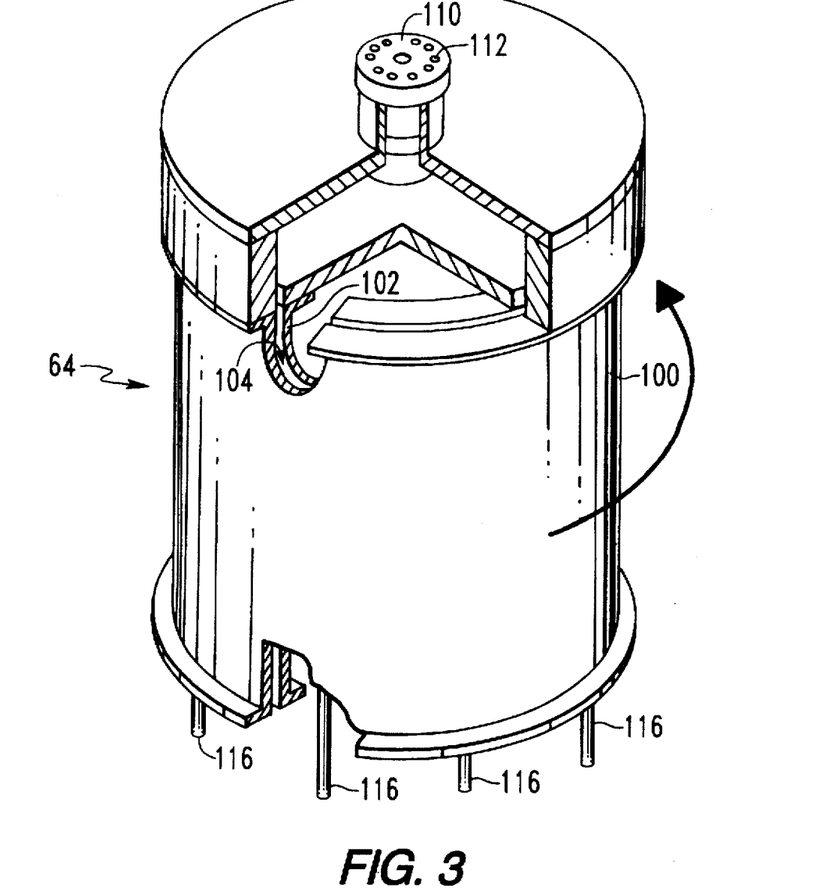

Referring again to the drawings, FIGS. 2 and 3 show a the continuous annular chromatograph (CAC) (64) preferred for use in the method and system of the present invention. A detailed description of the materials of construction, design, and operation of a CAC can be found in the earlier mentioned U.S. patents which are incorporated by reference herein in their entireties. A particularly preferred continuously operating chromatograph is the continuous annular chromatograph developed by Oak Ridge National Laboratory.

Such a CAC device (64) comprises two concentric cylinders (100) and (102) which define an annular column (104) which is rotated about an axis (106) of the annular column (104). The annular column (104) includes a stationary phase material, such as ion exchange resin beads (108), packed between the two concentric cylinders (100) and (102) of differing diameters with vertical axes to form the annular column. For ease of illustration, the ion exchange resin beads (108) are shown as only partially filling the annular column (104). One or more feedstock ports (110) is provided at a given angular position which supplies a feedstock solution to the ion exchange resin beads (108) which are packed in the annular column (104). One or more eluant ports (112) are provided at some angular offset from the feedstock port (110) which supplies an eluant to a layer of glass beads (114) which sit atop the resin beads (108). It is preferred to place a layer of glass beads (114) above the stationary phase material, and to feed the eluant on the top of the glass bead layer while feeding the crude aqueous, chloride-based zirconium/hafnium feedstock (40) directly to the top of the stationary phase to prevent any undesired mixing effects.

The CAC chromatograph (64) also includes a number of product delivery ports (116) set at different angular positions which can be set arbitrarily to accommodate particular operating conditions. Each product port (116) collects an elution volume containing a distinct product fraction which has had a particular residence time in the annular column (104) of the chromatograph (64). The CAC (64) is operated by rotating the annular column (104) packed with ion exchange resin beads (108) by a motor (not shown) at a constant speed so that any vertical segment of the annular bed is above a particular fixed product collection port (116) at a given time after this segment has been loaded with crude aqueous, chloride-based zirconium/hafnium feedstock (40) and eluant (66) solutions. Thus, each product collection port (116) has an angular position which corresponds to a particular elution time for a particular rate of rotation of the stationary phase resin beads (108) and for a particular flow rate through the stationary phase.

The flow rate through the stationary phase (108) is controlled by the pressure drop across the effective height of the stationary phase and the physical characteristics of the stationary phase, i.e., particle size and packing void volume. This pressure drop may be provided by the hydrostatic head of the feedstock and eluant, but it is preferably provided by pressurizing the device. The pressure required to achieve a particular flow rate is governed by the nature of the stationary phase (i.e., its packing, average particle size and particle size distribution). The smaller the average particle size of the resin beads making up the stationary phase, the larger the pressure drop required to obtain a particular flow rate over a particular effective height will be. However, the separation factor for any given theoretical stage is improved as the average particle size of the resin beads is decreased. Thus, the effective height needed to effect a given degree of separation is decreased as the separation capacity of a unit length (or theoretical stage height) is increased by decreasing the average particle size of the resin beads.

A short residence time in the chromatograph allows an increase in the zirconium and hafnium concentration in the product elution volumes. In general, the longer the residence time in the chromatograph is, the more "band spreading"

occurs. "Band spreading" is a term of art used in this context to describe the phenomenon that can be observed when the longer the residence time is, the larger the proportion of the total elution volume which contains some of the desired product. To obtain all or a certain percentage of this product fraction, it is necessary to collect a volume of eluant which increases with residence time. Thus, the net effect of band spreading is to dilute the zirconium and hafnium metal concentration in the product fractions.

The flow rate across the effective height of the stationary phase (108) and the rotational speed of the stationary phase should be coordinated so that a particular product fraction always elutes at the same angular position and, consequently, is always delivered to the same product collection port (116).

It is preferred that the chromatograph be operated in a displacement mode wherein no more than about 5 percent, more preferably no more than about 1 percent of the effective column height, is loaded with feedstock solution before elution is initiated. The angular displacement between the feed port and the eluant port and the speed of rotation of the annular bed are coordinated so that the time interval between loading and elution is just sufficient for the desired degree of penetration. The relationship between the time for loading and the depth of penetration is in turn governed by the flow rate through the annular bed.

The displacement may be effected by either an isocratic or a gradient supply of eluant. In the former case, the eluant can simply be supplied from a single port while in the latter case, several ports at successively greater angular displacements from the feed port are utilized. In the gradient mode, elution under the influence of the initial eluant is permitted to proceed until some separation has been effected, and then eluant with a higher concentration is supplied. This increases the migration speed down the column and minimizes the range of elution volumes or times over which a given component or product fraction will exit the column or, in other words, this procedure minimizes the band spreading. Further, by cooling the chromatographic column as well as the feedstock and/or eluant solutions, and waiting until the zirconium and hafnium wave fronts are sufficiently separated prior to gradient injection, the presence of a high free acid ($H^+$) concentration from the eluant does not induce cross-polymerization of the zirconium and hafnium in the column and further improves separation kinetics.

Decreasing the elution volumes by gradient elution or by other means increases the concentration of the product in the product fraction. Product concentrations greater than about 2 g/l, preferably greater than about 20 g/l, especially between about 20 and 70 g/l are preferred. It is preferred to maximize the concentration of product because the total volume of fluid to be processed will be reduced. This allows a reduction in the overall size of the system with a consequent reduction in capital and operating expenses. However, practical considerations, such as solubility limits, will constrain the maximum concentrations obtainable.

The flow rate down the chromatograph is governed by the pressure drop from the top to the bottom of the chromatograph and the nature of the stationary phase. The smaller the average particle size of the resin beads making up the stationary phase is, the higher the pressure drop that is required to obtain a given flow rate. This relationship is also affected by the particle size distribution of these resin beads. There is, however, a maximum attainable flow rate for any given resin stationary phase which cannot be exceeded by the application of additional pressure. The suppliers of such resins rate them in terms of flow rate per given pressure drop and maximum attainable flow rate.

It is preferred to use a stationary phase which will permit flow rates between about 2 and 80, more preferably between about 3 and 20 gallons per minute per square foot of cross sectional area (between about $1.36 \times 10^{-3}$ and $5.43 \times 10^{-2} m^3$/sec, more preferably between about $2.04 \times 10^{-3}$ and $1.36 \times 10^{-2} m^3$/sec per square meter of cross sectional area). There is a relationship between the achievable flow rates and the effective chromatograph column height needed for a given degree of purity. For a given system of stationary phase and eluant, the theoretical stage separation factor, $\alpha_s$, of the stationary phase will increase as the average particle size of the resin beads of the stationary phase decreases. However, as this particle size decreases, so does the flow capacity of the stationary phase. Thus, there is an inverse relationship between $\alpha_s$ and the flow capacity. A higher flow rate will require a greater effective column height to achieve the same degree of separation or product fraction purity.

Furthermore, there is the additional constraint that the pressure required to achieve the desired flow rate should not exceed the capability of available pumps, seals and feed tubing. The required pressure is a function of both the pressure drop needed per unit of effective height and the total effective height required for the desired degree of separation. Thus, as the flow capacity of the stationary phase is increased by a change in its physical configuration and, consequently, its theoretical stage separation factor, $\alpha_s$, is decreased, the required effective height and the required overall pressure drop are both increased. On the other hand, as the theoretical stage separation factor, $\alpha_s$, is increased by a change in the resin bead size distribution so that the flow capacity of the stationary phase is decreased, the pressure drop for a given effective height is increased. A preferred pressure drop of less than about 2759 kPa (400 psi), more especially between about 345 and 1042 kPa (50 and 150 psi), is preferred.

Thus, to obtain a system with a commercially practical capacity, it is necessary to use a stationary phase which will simultaneously display both a reasonable theoretical stage factor, $\alpha_s$, and a reasonable flow rate per unit of effective height with a reasonable pressure drop. This can be achieved by an appropriate selection of both the capacity of the stationary phase resin and eluant.

It is preferred that several product collection ports be used to collect a particular product fraction. This is accomplished by closely spacing these collection ports so that they more than span the angular range of rotation that corresponds to the elution time interval of that particular fraction, but do not extend to angular positions at which any significant portion of any other product fraction is expected to elute. Of course, this requires that the elution time intervals of different product fractions do not substantially overlap. That is, the alpha ($\alpha_s$) values should exceed 1, and should preferably be in the range of about 1.01 to 1.10, for all species. This arrangement tends to insure that minor fluctuations in the steady-state elution behavior which would cause a slight advancement or retardation of the elution time of the desired product fraction will not result in any loss of this fraction.

As the chromatograph rotates continuously, the product fractions in the feed are separated so that they are angularly displaced from the feed inlet. The four product fractions of primary concern are the zirconium fraction, the hafnium fraction, the heavy and transition metal waste fraction, and the radiochemical waste fraction. An additional product fraction also represents any miscellaneous product present in the feed solution which can be recycled to the column for further processing. The separated product fractions are collected in the collection vessels and processed further as described above.

Only a single continuous annular chromatograph has been described in connection with the present process. However, any number of continuous annular chromatographs may be employed in the present process. For example, two or three such chromatographs may be effectively used. Each chromatograph unit would require a supply of zirconium/hafnium feed and would produce the product fractions described above.

Table 3 below sets forth purely exemplary and non-limiting chromatographic operating conditions for achieving the efficient and effective separation and purification of zirconium and hafnium in accordance with the method and system of the present invention. Other examples and variations will be apparent from a consideration of the specification or from practice of the invention.

TABLE 3

Preferred Ion Exchange Chromatographic Operating Conditions

| | Range | Preferred |
|---|---|---|
| Feed Phase ($Zr$ and $Hf$ Ions) | | |
| Preparation Method | Two-Step Partial Hydolysis 0° C. to 110° C. | 10° C. to 25° C. |
| | One-Step Direct Hydrolysis 0° C. to 10° C. (Crushed Ice) | 0° C. to 5° C. |
| | Vapor Phase Hydrolysis 100° C. to 300° C. | 100° C. to 300° C. |
| Concentration | 50 to 200 g/l | 100 to 200 g/l |
| Solvent | Water | Water |
| For Cations | HCl | |
| Acid Concentration | 0 to 6N | 0 to 2N |
| For Anions | HCl | HCl |
| Acid Concentration | 0 to 5N | 0 to 2.5N |
| Stationary Phase (Ion Exchange Resin) | | |
| Type | Strong Acid or Weak Acid Cationic Exchange Resin; | ~1 gew/l |
| | Strong Base or Weak Base Anionic Exchange Resin | ~1 gew/l |
| Particle Size Mean Distribution Arbitrary | 01 to 500 microns Polydisperse to Monodisperse | <100 microns Monodisperse Spherical |
| Mobile Phase (Eluant) | | |
| Solvent | Water HCl | HCl |
| Acid Concentration | 1.0 to 5N | 1.5 to 2.5N for Zr Elution |
| | | 1.5 to 5N for Hf Elution |
| Elution Mode | Gradient and Isocratic | Gradient |
| Dissolution Temperature and Operating Temperature | 0° C. to 25° C. | 0° C. to 5° C. |

Industrial Applicability

The process of the present invention will find its primary application in the production of nuclear quality zirconium and hafnium metals and isotopically enriched zirconium and hafnium metals for nuclear reactor construction materials when it is desired to employ a simple, low cost process for the separation and purification of zirconium and hafnium and isotopes thereof.

The invention having been disclosed in connection with the foregoing variations and examples, additional variations and examples will now be apparent to persons skilled in the art. The invention is not intended to be limited to the variations and examples specifically mentioned, and accordingly reference should be made to the appended claims, to assess the spirit and scope of the invention in which exclusive rights are claimed.

We claim:

1. A continuous method for separating and purifying zirconium and hafnium comprising the steps of:
   (a) preparing an aqueous chloride feedstock solution of zirconium and hafnium ions while controlling the solution temperature to inhibit production of inseparable zirconium and hafnium copolymer complexes;
   (b) loading the aqueous chloride feedstock solution to a continuous ion exchange chromatographic column containing an ion exchange resin;
   (c) feeding an aqueous chloride eluant to the column to elute the feedstock solution from the ion exchange resin; and,
   (d) separately collecting a substantially pure zirconium fraction, a substantially pure hafnium fraction and at least one waste fraction.

2. The method of claim 1, in which step (a) further comprises:
   (i) chlorinating zircon sand in the presence of carbon to produce a crude $ZrCl_4$ and $HfCl_4$ fraction;
   (ii) partially hydrolyzing the crude $ZrCl_4$ and $HfCl_4$ fraction with water ($H_2O_{(l)}$) to produce a $ZrOCl_2$ and $HfOCl_2$ fraction and HCl fraction;
   (iii) controlling the temperature during step (ii) at about 10° to 25° C.,
   (iv) removing the HCl fraction for reuse;
   (v) dissolving the $ZrOCl_2$ and $HfOCl_2$ fraction in water to form the feedstock solution of zirconium and hafnium ions.

3. The method of claim 1, in which step (a) further comprises:
   (i) chlorinating zircon sand in the presence of carbon to produce a crude $ZrCl_4$ and $HfCl_4$ fraction;
   (ii) concurrently hydrolyzing and dissolving the crude $ZrCl_4$ and $HfCl_4$ fraction with crushed ice ($H_2O_{(s)}$) to form the feedstock solution of zirconium and hafnium ions; and,
   (iii) cooling as necessary to control the temperature during step (ii) to about 0° to 5° C.

4. The method of claim 1, in which step (a) further comprises:
   (i) chlorinating zircon sand in the presence of carbon to produce a crude $ZrCl_4$ and $HfCl_4$ fraction;
   (ii) subliming the $ZrCl_4$ and $HfCl_4$ fraction at a temperature of about 200° C. to 450° C. and a pressure of about 5 to 30 psi to form a $ZrCl_4$ and $HfCl_4$ vapor fraction;
   (iii) partially hydrolyzing the $ZrCl_4$ and $HfCl_4$ vapor fraction with steam ($H_2O_{(g)}$) to form a $ZrOCl_2$ and $HfOCl_2$ vapor fraction and an HCl vapor fraction;
   (iv) removing the HCl vapor fraction for reuse; and,
   (v) condensing the $ZrOCl_2$ and $HfOCl_2$ vapor fraction to an anhydrous $ZrOCl_2$ and $HfOCl_2$ fraction;
   (vi) dissolving the $ZrOCl_2$ and $HfOCl_2$ anhydrous fraction in water to form the feedstock solution of zirconium and hafnium ions.

5. The method of claim 1, in which said continuous ion exchange chromatographic column of step (b) is a continuous annular chromatographic column.

6. The method of claim 1, which further comprises:

(e) separately processing the zirconium fraction and the hafnium fraction to produce nuclear quality zirconium metal and hafnium metal;

(f) volume reducing the at least one waste fraction for disposal; and, (h) recycling the eluant for reuse in step (c).

7. The method of claim 1, in which the ion exchange resin is cationic or anionic exchange resin.

8. The method of claim 1, in which the aqueous chloride eluant comprises HCl.

9. The method of claim 1, which further comprises:

(e) separately processing the separated and purified zirconium fraction and hafnium fraction to produce isotopically enriched nuclear quality zirconium and hafnium by repeating steps (a) to (d) independently for each zirconium fraction and hafnium fraction.

10. The method of claim 1, which further comprises operating the column of step (b) at a temperature of about 0° C. to 5° C.

11. A continuous method for separating and purifying zirconium and hafnium comprising the steps of:

(a) preparing an aqueous chloride feedstock solution of zirconium and hafnium ions while controlling the solution temperature to inhibit production of inseparable zirconium and hafnium copolymer complexes;

(b) loading the aqueous chloride feedstock solution onto an ion exchange resin contained in a ion exchange chromatographic column of a continuous annular chromatograph;

(c) feeding an aqueous chloride eluant onto the ion exchange resin to elute the feedstock solution along the ion exchange chromatographic column of the continuous annular chromatograph;

(d) continuously rotating the continuous annular chromatograph during steps (b) and (c) while the aqueous chloride feedstock solution and the aqueous chloride eluant diffuse through the ion exchange resin;

(e) separately collecting a substantially pure zirconium fraction, a substantially pure hafnium fraction, and at least two waste fractions at collection locations on the continuous annular chromatograph angularly displaced from each other;

(f) separately processing the zirconium fraction and hafnium fraction to produce nuclear quality zirconium metal and hafnium metal; and, (g) recycling the aqueous chloride eluant for reuse in step (c).

12. The method of claim 11, which further comprises:

(h) collecting a mixed zirconium and hafnium fraction, loading said mixed fraction onto the ion exchange resin of step (b) and repeating steps (c) to (g).

13. The method of claim 11, in which step (a) further comprises:

(i) chlorinating zircon sand in the presence of carbon to produce a crude $ZrCl_4$ and $HfCl_4$ fraction;

(ii) partially hydrolyzing the crude $ZrCl_4$ and $HfCl_4$ fraction with water ($H_2O(l)$) to produce a $ZrCl_2$ and $HfOCl_2$ fraction and HCl fraction;

(iii) controlling the temperature during step (ii) to about 10° to 25° C.;

(iv) removing the HCl fraction for reuse;

(v) dissolving the $ZrOCl_2$ and $HfOCl_2$ fraction in water to form the feedstock solution of zirconium and hafnium ions.

14. The method of claim 11, in which step (a) further comprises:

(i) chlorinating zircon sand in the presence of carbon to produce a crude $ZrCl_4$ and $HfCl_4$ fraction;

(ii) concurrently hydrolyzing and dissolving the crude $ZrCl_4$ and $HfCl_4$ fraction with ice ($H_2O_{(s)}$) while controlling a temperature of the fraction to about 0° C. to 5° C. to form the feedstock solution of zirconium and hafnium ions.

15. The method of claim 11, in which step (a) further comprises:

(i) chlorinating zircon sand in the presence of carbon to produce a crude $ZrCl_4$ and $HfCl_4$ fraction;

(ii) subliming the $ZrCl_4$ and $HfCl_4$ fraction at a temperature of about 200° C. to 450° C. and a pressure of about 5 to 30 psi to form a $ZrCl$ and $HfCl_4$ vapor fraction;

(iii) partially hydrolyzing the $ZrCl_4$ and $HfCl_4$ vapor fraction with steam ($H_2O_{(g)}$) to from a $ZrOCl_2$ and $HfOCl_2$ vapor fraction and an HCl vapor fraction;

(iv) removing the HCl vapor fraction for reuse; and, (v) condensing the $ZrOCl_2$ and $HfOCl_2$ vapor fraction to an anhydrous $ZrOCl_2$ and $HfOCl_2$ fraction;

(vi) dissolving the $ZrOCl_2$ and $HfOCl_2$ anhydrous fraction in water to form the feedstock solution of zirconium and hafnium ions.

16. The method of claim 11, which further comprises operating the continuous annular chromatograph of step (b) at a temperature of about 0° C. to 5° C.

17. The method of claim 11, in which the aqueous chloride eluant comprises HCl.

18. The method of claim 11, in which the zirconium fraction collected in step (e) has a concentration of greater than about 10 g/l, a purity of less than 100 ppm Hf in the zirconium product fraction, and a yield of greater than about 50%.

19. The method of claim 18, in which the method is performed in a single pass through the continuous annular chromatograph of step (c).

20. The method of claim 11, in which the zirconium fraction collected in step (e) has a concentration of greater than about 15 g/l, a purity of less than about 50 ppm Hf in the zirconium product fraction, and a yield of greater than about 90%.

* * * * *